US011707055B2

(12) United States Patent
Du et al.

(10) Patent No.: US 11,707,055 B2
(45) Date of Patent: Jul. 25, 2023

(54) LARVAE COUNTER

(71) Applicants: ORINNO TECHNOLOGY PTE. LTD., Singapore (SG); NATIONAL ENVIRONMENT AGENCY, Singapore (SG)

(72) Inventors: Yu Du, Singapore (SG); Lu Deng, Singapore (SG)

(73) Assignees: ORINNO TECHNOLOGY PTE. LTD., Singapore (SG); NATIONAL ENVIRONMENT AGENCY, Singapore (SG)

( * ) Notice: Subject to any disclaimer, the term of this patent is extended or adjusted under 35 U.S.C. 154(b) by 815 days.

(21) Appl. No.: 16/643,379

(22) PCT Filed: Aug. 29, 2018

(86) PCT No.: PCT/SG2018/050436
§ 371 (c)(1),
(2) Date: Feb. 28, 2020

(87) PCT Pub. No.: WO2019/045648
PCT Pub. Date: Mar. 7, 2019

(65) Prior Publication Data
US 2020/0359608 A1   Nov. 19, 2020

(30) Foreign Application Priority Data

Aug. 30, 2017  (SG) ........................... 10201707072X

(51) Int. Cl.
*A01K 61/90*     (2017.01)
*A01K 63/06*     (2006.01)
(Continued)

(52) U.S. Cl.
CPC ............ *A01K 61/90* (2017.01); *A01K 63/065* (2013.01); *A01K 67/033* (2013.01); *G01D 5/342* (2013.01); *G06M 7/00* (2013.01); *G06M 11/00* (2013.01)

(58) Field of Classification Search
CPC .... A01K 61/90; A01K 63/065; A01K 67/033; G01D 5/342; G06M 7/00; G06M 11/00
See application file for complete search history.

(56) References Cited

U.S. PATENT DOCUMENTS

| 4,743,742 A   | * | 5/1988 | Espedalen ............... G06M 7/00 377/6 |
| 5,594,654 A   |   | 1/1997 | Shuman et al. |
| 10,398,133 B2 | * | 9/2019 | Hilmarsson ............ A01K 61/10 |

FOREIGN PATENT DOCUMENTS

| CN | 102805044 A | 12/2012 |
| KR | 10-2012-0034408 A | 12/2012 |

(Continued)

OTHER PUBLICATIONS

Simonet D.E. et al., "A Biomonitoring Procedure Utilizing Negative Phototaxis of First Instar Aedes aegypti larvae", Arch Environ Contam Toxicol., Dec. 1, 1978, vol. 7, No. 1, pp. 339-347.

(Continued)

*Primary Examiner* — Seung C Sohn
(74) *Attorney, Agent, or Firm* — Burns & Levinson LLP; Steven M. Mills

(57) ABSTRACT

A larvae counter comprising a first container for receiving water, eggs of insects and/or larvae, a second container in fluid communication with the first container for receiving water and larvae from the first container, and a larvae counting module in fluid communication with the second container for receiving water and larvae from the second container and counting the larvae.

20 Claims, 3 Drawing Sheets

(51) Int. Cl.
  *A01K 67/033*  (2006.01)
  *G01D 5/34*  (2006.01)
  *G06M 7/00*  (2006.01)
  *G06M 11/00*  (2006.01)

(56) References Cited

FOREIGN PATENT DOCUMENTS

| | | |
|---|---|---|
| WO | 2011106119 A2 | 9/2011 |
| WO | 2013080351 A1 | 6/2013 |

OTHER PUBLICATIONS

Carron A. et al., "An Easy Field Method for Estimating the Abundance of Culicid Larval Instars.", J Am Mosq Control Assoc., Dec. 1, 2003, vol. 19, No. 4, pp. 353-360.
PCT Search Report & Written Opinion for PCT Application No. PCT/SG2018/050436 dated Dec. 13, 2018, 12 pages.

* cited by examiner

LARVAE COUNTER

CROSS REFERENCE TO RELATED APPLICATIONS

This application is a national stage application, filed under 35 U.S.C. § 371, of International Application No. PCT/SG2018/050436, filed Aug. 29, 2018, which claims priority to SG 10201707072X, filed Aug. 30, 2017, each of which is incorporated herein by reference in its entirety.

FIELD OF THE INVENTION

The present invention relates to a larvae counter for counting larvae in a water body. In particular, the present invention relates to a larvae counter for counting larvae in a water body and a method of counting larvae in a water body.

BACKGROUND

Mosquitos are ubiquitous type of insect present in many countries. For some species of mosquitos, female mosquitos feed on humans. Female mosquitos are vectors for a number of infectious diseases which affect millions of people every year. The issue of a growing mosquito population is worrying.

Several methods are known to count and estimate the abundance of larvae within a breeding habitat. However, many of such methods are carried out manually using sampling methods. Such methods are often inaccurate and labour intensive.

It is therefore desirable to provide an apparatus and a method that seeks to address at least one of the problems described hereinabove, or at least to provide an alternative.

SUMMARY OF INVENTION

In accordance with one aspect of this invention, a larvae counter is provided. The larvae counter comprises a first container for receiving water, eggs of insects and/or larvae, the first container having an outlet for dispensing larvae and water from the first container; a second container in fluid communication with the first container for receiving larvae and water from the first container; and a larvae counting module in fluid communication with the second container for receiving larvae from the second container and counting the larvae; wherein the second container comprises a channel in fluid communication with the larvae counting module, the channel configured for directing larvae from the second container into the larvae counting module; and wherein the larvae counting module comprises a passage for single larva to pass through and a detector positioned proximate the passage for detecting each larva passing through the passage.

In one embodiment, the channel is configured to direct larva one at a time from the second container into the passage of the larvae counting module.

In one embodiment, the larvae counting module comprises a funnel having an upper portion and a lower portion, the upper portion being wider than the lower portion, the lower portion defines the passage for single larva to pass through and wherein the lower portion has an open end for water and larvae to pass through and out of the larvae counter after the larvae are counted.

In one embodiment, the second container further comprises a water inlet positioned at the top of the second container for receiving water and larvae from the first container. The second container is in fluid communication with the first container via a conduit, wherein the conduit comprises a first end and a second end, the first end having a funnel mouth for receiving larvae and water from the first container and the second end is removably attached to the water inlet of the second container.

In one embodiment, the first container is provided with at least one light source positioned at the bottom of the first container for stimulating larvae to separate from the eggs.

In one embodiment, the second container is provided with a plurality of light sources positioned along the side walls of the second container and/or the bottom of the second container for controlling larvae distribution inside the second container.

In one embodiment, the larvae counting module is provided with at least one light source positioned along the passage.

In one embodiment, the first container, the second container, the channel and the lower portion of the larvae counting module defining the passage are each provided with at least one valve for regulating the flow rate of water and larvae movement from one place to another.

In accordance with a second aspect of this invention, a method for counting larvae is provided. The method comprises providing a first container to receive water, eggs of insects and/or larvae; transferring the water with larvae from the first container into a second container; stimulating the larvae in the second container using at least one light source to guide the larvae to pass through an outlet of the second container and into a channel connected to the outlet of the second container; directing the larvae in the channel into a larvae counting module; directing the larvae through a passage in the larvae counting module one at a time; detecting each larva passing through the passage; and counting each larva passing through the passage.

In one embodiment, the method further comprises stimulating the larvae in the first container to move towards an outlet of the first container using at least one light source positioned at the bottom of the first container.

In one embodiment, the water and the larvae from the first container are transferred to the second container by a conduit connected to the second container.

In one embodiment, the method further comprises placing the first container at a higher level than the second container, and placing the second container at a higher level than the larvae counting module for enabling gravity induced flow of water and larvae from the first container into the second container and from the second container into the larvae counting module.

In one embodiment, the stimulation of the larvae in the second container comprises placing a plurality of light sources along the side walls and the bottom of the second container, with the number of light sources at the bottom being fewer than the plurality of light sources placed along each of the side walls to encourage the larvae to move towards the water outlet of the second container.

In one embodiment, the method further comprises controlling the flow of water and larvae in the channel and into the passage using an outlet valve positioned at the channel.

In one embodiment, the method further comprises controlling the flow of water and larvae in the passage using a second outlet valve positioned at the passage of the larvae counting module.

In one embodiment, the method further comprises stimulating the larvae in the larvae counting module using at least one light source positioned along the passage of the larvae counting module.

In one embodiment, the method further comprises regulating the flow of water and larvae from one place to another place by controlling at least one valve provided at each of the first container, the second container, the channel and the passage.

BRIEF DESCRIPTION OF THE DRAWINGS

The accompanying figures (Figs.) illustrate embodiments and serve to explain principles of the disclosed embodiments. It is to be understood, however, that these figures are presented for purposes of illustration only, and not for defining limits of relevant inventions. Particularly.

DETAILED DESCRIPTION

The present invention aims to provide a useful larvae counter for counting larvae in a water body and a method of using the same. Exemplary, non-limiting embodiments of the present application will now be described with references to the above-mentioned figures.

Figure 1:
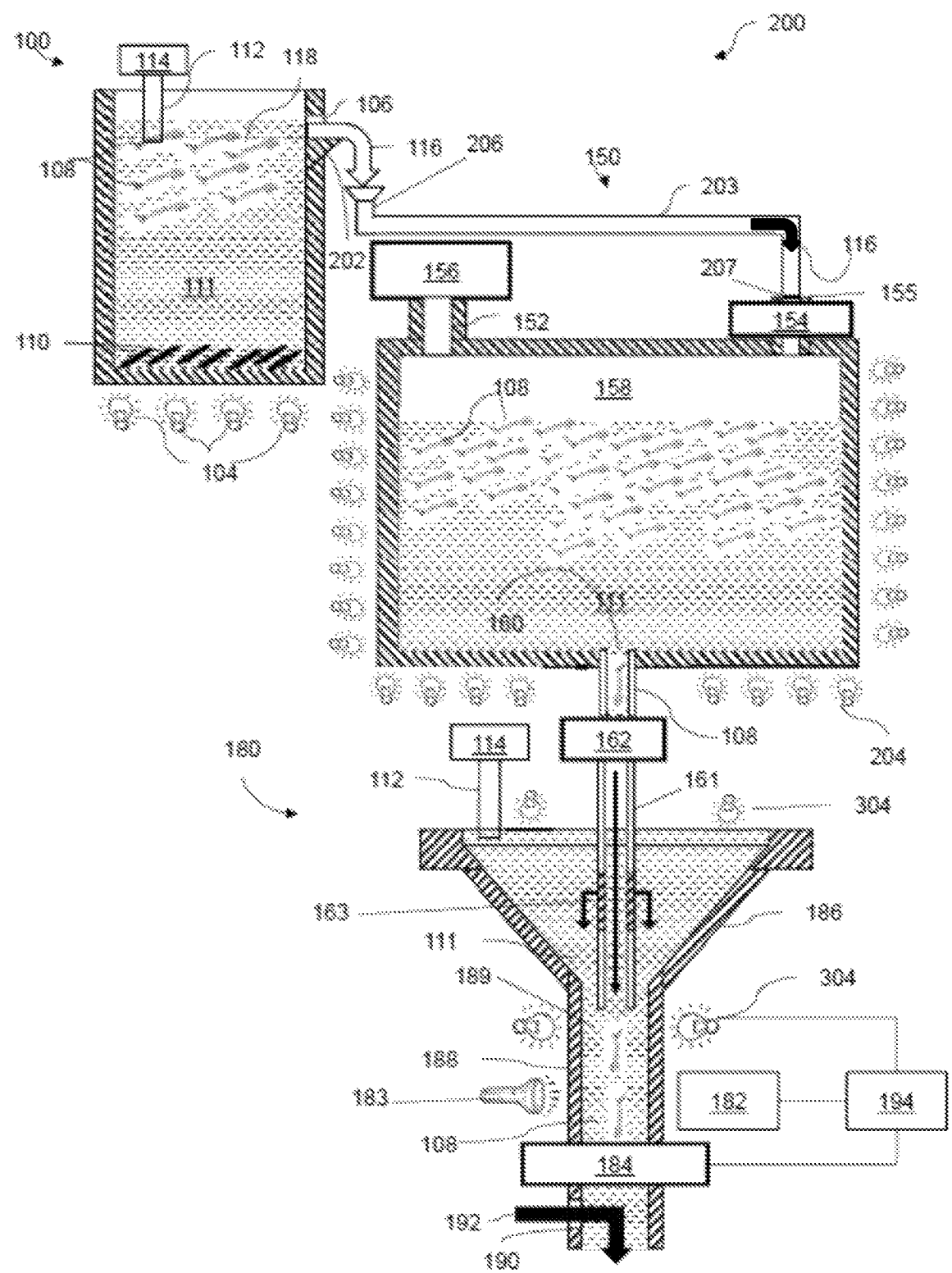
FIG. 1 illustrates a larvae counter according to a preferred embodiment of the present invention.

FIG. 1 illustrates a larvae counter in accordance with an embodiment of the present invention. The larvae counter 200 comprises a first container 100 for receiving water, eggs of insects and/or larvae, the first container having an outlet for dispensing water and larvae from the first container; a second container 150 in fluid communication with the first container for receiving larvae and water from the first container; and a larvae counting module 180 in fluid communication with the second container for receiving larvae from the second container and counting the larvae. The second container comprises a channel in fluid communication with the larvae counting module. The channel is configured for directing larvae from the second container into the larvae counting module. The larvae counting module comprises a passage for single larva to pass through and a detector positioned proximate the passage for detecting each larva passing through the passage and counting the larvae.

Figure 2:
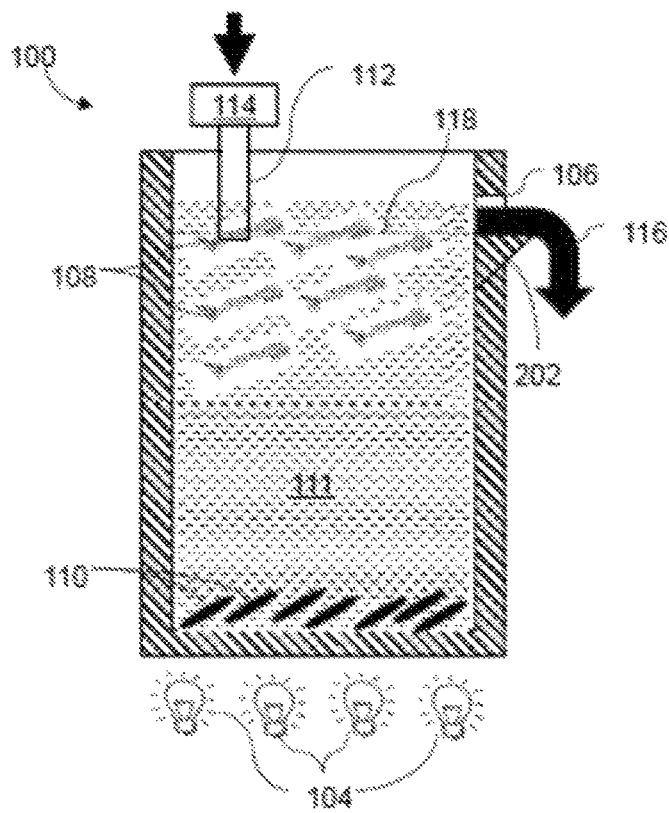
FIG. 2 illustrates a first container for hatching eggs of mosquitos into larvae according to an embodiment of the present invention.

FIG. 2 illustrates a cross-sectional view of the first container 100.

The first container 100 is a hollow cylindrical container with an open top. The first container 100 comprises an aperture 106 disposed proximate the open top of the first container 100. The aperture 106 is provided for dispensing water and larvae from the first container. The aperture 106 can be configured into any suitable form for dispensing water and larvae from the first container. In one embodiment, the aperture 106 is provided with a displacement spout 202 located at the mouth of the aperture 106 for directing water and larvae from the first container into the second container. In another embodiment, the aperture 106 is fitted with a hose or pipe for directing water and larvae from the first container to the second container.

The first container 100 further comprises a water inlet 112 and a water inlet valve 114. In one embodiment, the water inlet 112 and the water inlet valve 114 are located at the brim of the open top of the first container 100. The water inlet 112 has a duct for channelling water into the first container 100. Preferably, the duct of the water inlet 112 has a length sufficient to extend below a water displacement line 118 of the first container when the first container is filled with water. This is to allow water to flow into the first container while maintaining a ripple free water surface. The rate of flow of water through the water inlet 112 is controlled by the water inlet valve 114. A water flowmeter (not shown) may be installed to quantify the flow rate through the water inlet 112. The flow rate is measured in milliliters per second (ml/s).

In one embodiment, the first container 100 has a circular bottom and a circular top. This is to prevent larvae from clustering at a corner of the first container 100. The first container 100 has a smooth inner periphery wall. The smooth inner periphery wall serves the same purpose of preventing larvae from forming a cluster around the corners of the first container or clinging onto and clustering near the inner periphery wall of the first container. The physical structure of certain species of larva has brushes and spiracles extending from its body. It is therefore advantageous for the first container 100 to have smooth inner periphery wall and void of orthogonal corners so as to prevent the larvae from clustering around the corners of the first container 100. The smooth inner periphery wall of the first container is opaque. This is to create a darker environment within the first container 100. The bottom of the first container is transparent. This is to facilitate propagation of light beams into the first container 100 through the bottom of the first container for stimulating separation of larvae from the eggs. The first container 100 further comprises a lid (not shown). The lid is opaque. The lid provides a covering for the first container 100 to create a dark, undisturbed environment for larvae in the first container to live. One skilled in the art will understand and appreciate that the lid can be of any suitable form, size and shape without departing from the scope of the present invention.

The first container 100 is provided for receiving water, eggs of insects and/or larvae. When there are eggs of insects in the water in the first container, the first container 100 provides an environment for incubating and/or hatching the eggs of insects into larvae. After the eggs are hatched, the first container 100 provides an environment for segregating the eggs and the hatched larvae. In one embodiment, the segregation of eggs and larvae is carried out by providing a plurality of light sources 104 and arranging the plurality of light sources 104 along the bottom of the first container 100. The light beams from the plurality of light sources 104 propagate through the bottom of the first container and into the first container 100. Larvae generally are attracted to dark areas in an environment. When the plurality of light sources 104 shines through the bottom of the first container 100, the light beams from the plurality of light sources 104 stimulate the larvae in the water and causes the larvae to wriggle upwards towards the open top of the first container. The plurality of light sources 104 may further provide temperature control to accelerate the growth of larvae in the first container 100.

Light acts as environmental signal to control larvae behaviour at various levels. The amount of light entering the first container 100 is controlled by the number of light sources 104 arranged along the bottom of the first container. To impede or reduce the amount of light from entering the first container 100, an opaque adhesive sheet is applied onto the outer periphery side walls of the first container 100.

The first container 100 is in fluid communication with the second container 150. In one embodiment, the first container 100 is in fluid communication with the second container 150 via a conduit 203. The conduit 203 has a first end 206 and a second end 207. The first end 206 of the conduit is configured for receiving water and larvae from the first container 100. Any suitable configuration of the first end 206 of the conduit can be employed without departing from the scope of the present invention. In one embodiment, the first end 206 of the conduit has a wide funnel mouth for receiving water and larvae dispensed from the first container 100. The second end 207 of the conduit is removably attached to a water inlet 155 of the second container. In one embodiment, the conduit 203 is a cylindrical pipe made of clear, transparent material. Suitable material includes, but is not limited to, glass and plastics. One skilled in the art will appreciate that other suitable type of conduit may be employed without departing from the scope of the present invention. In one embodiment, the conduit 203 is positioned titled at an angle with respect to a horizontal plane to aid in the transfer of water and larvae from the first container to the second container. The titled configuration of the conduit 203 also prevents stagnation of water within the conduit 203.

Figure 3:
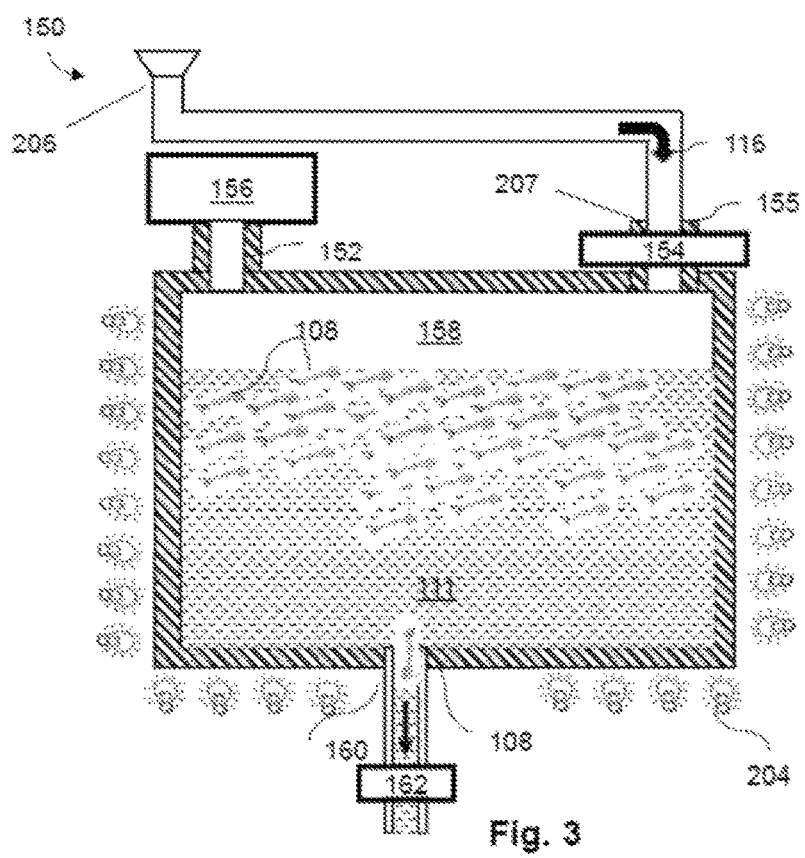
FIG. 3 illustrates a second container for receiving and holding larvae from the first container according to an embodiment of the present invention.

FIG. 3 illustrates a cross-sectional view of the second container 150.

The second container 150 is an airtight cylindrical drum providing a receptacle for receiving water and larvae in a pressurised air environment. In one embodiment, the primary function of the second container 150 is for controlling the distribution of larvae in the larvae counter 200. The second container 150 comprises an air inlet 152, a needle valve 156, a water inlet 155, a water inlet valve 154, a water outlet 160 and a water outlet valve 162. In one embodiment, the air inlet 152 and the water inlet 155 are positioned opposite the water outlet 160. The needle valve 156 is positioned above the air inlet 152. The water inlet valve 154 is positioned proximate the water inlet 155.

The water inlet valve 154 regulates the volume of water flowing into the second container 150 through the water inlet 155. When the second container 150 is filled with water, an air pocket 158 above the water within the second container 150 is created. The needle valve 156 controls the amount of air entering the second container 150 through the air inlet 152 and regulates the air pressured within the second container 150. The air pocket 158 is created for providing fresh air supply to the larvae held inside the second container. The needle valve 156 also controls the flow rate of water out from the second container 150 via the water outlet 160.

The second container 150 is provided with a plurality of light sources 204 strategically arranged and spaced along the external walls of the second container 150. The external walls include the two side walls and the bottom of the second container. The plurality of light sources 204 are provided for stimulating and controlling the movement of the larvae in the second container 150. In one embodiment, the plurality of light sources 204 arranged at the bottom of the second container is fewer than the plurality of light sources 204 arranged at the side walls of the second container. Larvae are generally attracted to dark areas in an environment. As such, the fewer light sources at the bottom of the second container will encourage the larvae to move towards the base of the second container where the water outlet 160 is positioned. No light source is provided at the top of the second container 150 as larvae in the second container 150 will instinctively wriggle towards the top of the second container for respiration. The water outlet 160 of the second container 150 is located at the base of the second container 150. The diameter of the water outlet 160 should be wide enough for a specific range of sizes of larvae to pass through.

The second container 150 further comprises a channel 161 extending perpendicularly from the water outlet 160 of the second container. In one embodiment, the channel 161 is removably attached to the water outlet 160 of the second container. In another embodiment, the channel 161 forms an integral part of the second container. The channel 161 is an elongated pipe or tube configured for directing larvae from the second container 150 into the larvae counting module 180. The diameter of the channel should be narrow enough to allow one larva to pass through the channel 161 and into the larvae counting module. In one embodiment, the channel 161 has a cross-sectional diameter of 1.0 mm to 6.0 mm. The channel 161 comprises a plurality of openings 163 disposed along the longitudinal surface of the channel that is away from the water outlet 160. When the channel 161 is in fluid communication with the larvae counting module 180, the plurality of openings 163 are positioned within the larvae counting module 180. The water outlet valve 162 is positioned in the fluid passage of the channel 163 and operative to regulate the flow of water through the channel 163 and into the larvae counting module.

Figure 4:
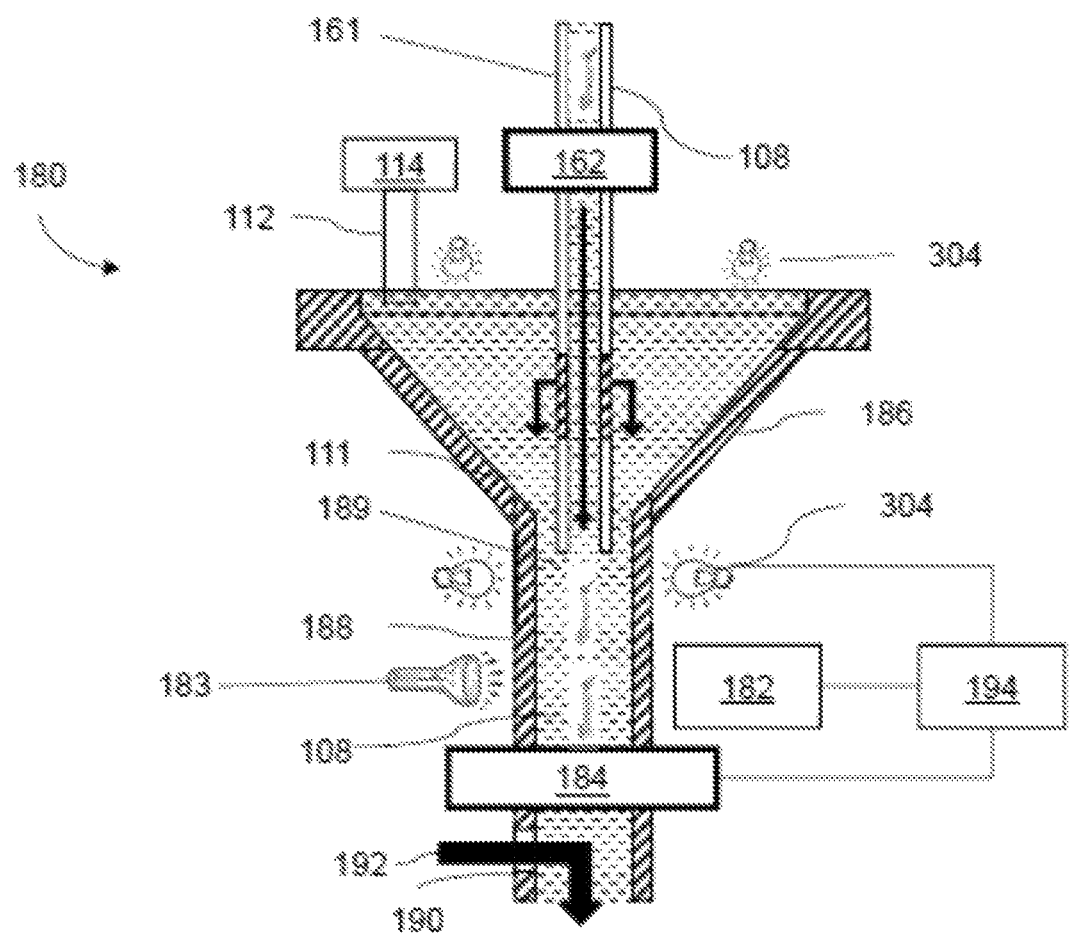
FIG. 4 illustrates a larvae counting module of the larvae counter according to an embodiment of the present invention.

FIG. 4 illustrates a cross sectional view of the larvae counting module 180.

The larvae counting module 180 comprises a funnel having an upper portion 186 and a lower portion 188, the upper portion being wider than the lower portion. The upper portion 186 is configured for receiving water from the second container 150. The lower portion 188 defines a passage 189 for water and larvae to pass through and to be counted. In one embodiment, the lower portion 188 of the larvae counting module is about 100 mm to 1,000 mm in length, with a cross-sectional diameter of about 1.0 mm to 6.0 mm.

The larvae counting module 180 further comprises a water inlet 112, a water inlet valve 114, a water outlet 190 and a water outlet valve 184. In one embodiment, the water inlet valve 114 is positioned in the fluid passage of the water inlet 112. The water outlet 190 is positioned at bottom end of the lower portion 188 of the larvae counting module 180. The water outlet valve 184 is positioned in the fluid passage of the passage 189 at the lower portion 188 of the larvae counting module 180. The water outlet valve 184 is operative to regulate flow of water out of the larvae counting module 180.

The larvae counter 200 further comprises a detector 182. The detector 182 detects, identifies, tracks and counts the larvae that pass through the passage 189. In one embodiment, the detector 182 is positioned on one side of the passage 189 and above the water outlet valve 184. The detector 182 can be any suitable type of detector 182. In one embodiment, the detector 182 is an image capturing device that includes an image sensor. The image sensor detects and conveys information that constitutes an image of a larva and a length of the larva. One example of the detector 182 is a charge-coupled device (CCD) image sensor on a flexible circuit board. In another embodiment, the detector 182 comprises an optical counter or a particle counter for detecting each larva that passes through the passage of the larvae counting module. In one embodiment, the optical counter comprises a light sensor for detecting change of intensity of light as larvae passes through the detector. Suitable light sensors include, but are not limited to, photomultiplier tube (PMT), photodiode and avalanche photodiode (APD)s. In another embodiment, the optical counter may comprise a laser sensor for sensing change of laser as affected by passing larvae.

The larvae counter 200 further comprises a counter light source 183. In one embodiment, the counter light source 183 is positioned on another side of the passage 189, opposite the detector 182 such that the passage 189 is interposed between the counter light source 183 and the detector 182. The counter light source can be any suitable type of light source including, but not limited to, laser diode, injection laser diode, light-emitting diode (LED) and light source with mechanical shutters for modulating light intensity.

The larvae counting module 180 is further provided with a plurality of light sources 304. The plurality of light sources 304 is arranged along the external walls of the lower portion 188 of the larvae counting module and/or above the upper portion 186 of the funnel of the larvae counting module. The plurality of the light sources 304 stimulates the movement of larvae in the larvae counting module towards the passage 189.

The larvae counter 200 further comprises a processor unit 194. The processor unit 194 is capable of comparing larvae that passes through the passage 189 with a preset specification, for example, the size and the length, of a desired larva.

The processor unit 194 is a microcontroller surface mounted on a printed circuit board. The processor unit 194 comprises memory storage, a processing chip and a plurality of input and output channels providing interface to the external peripherals. The processor unit 194 is electrically powered. The processor unit 194 is connected to the plurality of light sources 104, 204, 304, the water inlet valves 114, 154, 162, 184 and the detector 182. In one embodiment, the connections are made of metallic wire fabricated onto a printed circuit board. The ends of the connections can be insulated wires extending from the soldering pads on the printed circuit board. One skilled in the art will appreciate that other suitable type of connections can be employed without departing from the scope of the present invention. The processor unit 194 has a plurality of algorithm to control the operation of the plurality of light sources 104, 204, 304 and the water inlet valves 114, 154, 162, 184. The processor unit 194 keeps track and counts the larvae as each larva passes through the passage 189 of the larvae counting module to be counted. For example, based on the detection of the one larva by the detector 182 and the counter light source 183, the processor unit 194 keeps count and stores the count in the memory storage thereof.

In one embodiment, the plurality of light sources 104, 204, 304 are light emitting diodes (LED) with a light output of about 200 lumens, consuming about 3 Watts of electrical power for each LED. The plurality of light sources 104, 204, 304 is strategically positioned to stimulate and drive the larvae to wriggle to specific areas of the first container, the second container and the larvae counting module in the water. The plurality of light sources 104, 204, 304 provides control over the movement (to gather or disperse) of larvae in the first container 100, the second container 150 and the larvae counting module 180 by alternating the light intensity and frequency of the light sources 104, 204, 304. The plurality of light sources 104, 204, 304 may be strobing at a regular frequency or completely on or off. The plurality of light sources 104, 204, 304 can be dimmed or completely lit as desired.

In one embodiment, the water inlet valves 114, 154, 162, 184 are a 2-way solenoid valve, for example, valve with two ports. A solenoid valve is an electromechanically operated valve. The valve is controlled by an electric current through a solenoid in the case of a two-port valve. If a valve is opened, the two ports are connected and the fluid (liquid, gas) may flow between the two ports. If the valve is closed, then the ports are isolated. The valves 114, 154, 162, 184 are at a normal closed state.

The water inlet valves 114, 154, 162, 184, the plurality of light sources 104, 204, 304, the detector 182, the processor unit 194 and the counter light source 183 are electrically powered. The power supply (not shown) is from the utility which is then stepped down and converted (AC to DC) to a Direct Current (DC) supply.

In one embodiment, the larvae counter 200 of the present invention uses gravitational force to effect the flow of water from a higher level to a lower level. In this embodiment, the first container 100 is positioned at a level higher than the second container 150 and the second container 150 is positioned at a level higher than the larvae counting module 180. The arrangement of the first container, the second container and the larvae counting module in this manner initiates water flow from the first container to the second container and to the larvae counting module.

The first container, the second container and the larvae counting module are made of suitable transparent material. Such material includes, but is not limited to, glass, clear plastics, and the like. Suitable plastics include, but not limited to, poly(methyl methacrylate) (PMMA). The use of plastic prevents breakage, and therefore reduces injuries and/or accidents. Preferably, the material is transparent enough for light beams from the light sources 104, 204, 304 to penetrate the walls of the first container, the second container and the larvae counting module. The material should have a thickness sufficient to support the contents in the first container, the second container and the larvae counting module and sufficient for light beams from the light sources 104, 204, 304 to penetrate the material and into the first container, the second container and the larvae counting module. In one embodiment, the material has a thickness of about 1 to 2 mm, preferably 1 to 1.5 mm.

Preferably, the first container 100, the second container 150 and the larvae counting module 180 are not an integral unit. The first container, the second container and the larvae counting module are separate units so as to provide a modularised construction and hence portability. The first container 100, the second container 150 and the larvae counting module 180 can each be removed from the larvae counter when the rearing of the larvae is to cease for disposal.

The term "disposal" is used herein to include the release of larvae from the larvae counter or destruction of the larvae.

The separate units of the first container 100, the second container 150 and the larvae counting module 180 allow simple maintenance and troubleshooting of the larvae counter. Maintenance of the larvae counter includes washing or repairing of the first container 100, the second container 150 and the larvae counting module 180.

In one embodiment, the larvae counter of the present invention comprises at least one valve connected to each of the first container, the second container and the larvae counting module for regulating the flow rate of water in the larvae counter. The at least one valve includes water inlet valve, water outlet valve or a combination of both. In the embodiments described hereinabove, the primary function of the water inlet valves 114, 154, 162, 184 is to regulate the flow of water within the larvae counter. The regulation of the water flow provides a control of larvae movement from one container to another container. The regulation of the water flow also provides a control over the concentration of larvae present in body of water. The flow regulation can either be an open position or a close position.

In accordance with a second aspect of the present invention, a method for counting larvae is provided. The method comprises providing a first container to receive water, eggs of insects and/or larvae; transferring the water with larvae from the first container into a second container; stimulating the larvae in the second container using at least one light source to guide the larvae to pass through an outlet of the second container and into a channel connected to the outlet of the second container; directing the larvae in the channel into a larvae counting module; directing the larvae through a passage in the larvae counting module one at a time; detecting each larva passing through the passage; and counting each larva passing through the passage.

In one embodiment, the first container 100 is provided to receive water, providing a conducive environment for female insects to lay eggs 110 or for direct placement of eggs of insects by a human. In another embodiment, the first container is provided to receive water and eggs of insects. In yet another embodiment, the first container is provided to receive water and larvae. In yet a further embodiment, the first container is provided to receive water, eggs of insects and larvae.

The term "water" is used herein to refer to water that is clear, pH (potential of hydrogen) neutral and at room temperature. The water used in the present invention should provide conditions suitable for rearing eggs of insects and larvae.

In one embodiment, the first container 100 is filled with water flowing in from the water inlet 112 until the water overflows through the aperture 106. Upon reaching the water displacement line 118, the water inlet valve 114 is shut to stop the water flow from the water inlet 112.

Larvae live in still water. Therefore, the water in the first container should be relatively still with minimal water ripples on the surface. This can be achieved by keeping the flow rate of the incoming water relatively low to maintain a ripple free water surface. The water in the first container should also be relatively clear so as to differentiate the eggs 110 from the larvae 108 swimming in the body of water and/or to differentiate the larvae 108 from suspension in the body of water. In the embodiments wherein the water contains eggs of insects, the eggs 110 will settle at the bottom of the first container 100 as shown in FIG. 1.

In the embodiments wherein the water contains eggs of insects, the method may comprise incubating and hatching the eggs into larvae in the first container. The method may further comprise placing the eggs 110 on the surface of the water in the first container for incubating and hatching. For eggs of mosquitoes, within one to three days, the embryonic development is completed in an egg, and a larva (which is also known as "wriggler") hatches out from the egg. When a larva first hatches out, the length of the larva is about 1 mm long and transparent. The hatched larvae actively swim in the water by wriggling, feeding upon aquatic micro-organisms at the bottom of the first container, and grow by undergoing four molts (shedding old exoskeleton). Some species of larvae feed upon the surface of the water surface. In the embodiment wherein the eggs are laid by female mosquitoes, not by direct placement of the eggs by human, the eggs will hatch within 24-48 hours after the eggs are laid. The average length of a larva is about 3 mm.

Depending on the size of the larvae when the larvae mature, the species of the larvae and the water temperature, the method may comprise covering the first container with the lid to provide a dark environment within the first container to encourage the growth of the larvae. The method of the present invention may further include segregating the larvae and the eggs in the first container and directing the larvae to move towards the aperture 106 of the first container. The method comprises stimulating the larvae in the first container to move towards the aperture 106 of the first container. In one embodiment, the stimulation is carried out by using at least one light source positioned at the bottom of the first container. FIG. 1 shows an exemplary embodiment whereby a plurality of the light sources 104 are arranged at the bottom of the first container. The plurality of light sources 104 provides an illumination of the water 111 and drives the larvae 108 at the bottom of the first container to wriggle upwards, towards the surface of the water 111 to where the aperture 106 is located.

The plurality of light sources 104 may also provide a source of heat to speed up the larvae growth. If this application is desired, the plurality of light sources 104 can be changed to a higher power rated LED or to halogen light bulbs. The plurality of light sources 104 are arranged uniformly according to the light coverage around the bottom of the first container 100.

When the plurality of light sources 104 arranged at the bottom of the first container 100 is switched on, the light beams from the plurality of light sources 104 penetrate the bottom of the first container and drive the larvae 108 towards the surface of the water 111 where the aperture 106 is located. The water inlet valve 114 of the water inlet 112 is then turned on to allow more water to flow into the first container 100, causing a water displacement through the aperture 106. The displaced water 111 containing the larvae flows out from the aperture 106 (as shown by arrow 116 in FIG. 1) and into the first end 206 of the conduit 203.

The water and larvae trickled from the first container 100 flows through the conduit 203, through the water inlet 155 and into the second container 150. The larvae 108 wriggle inside the second container 150. The plurality of light sources 204 arranged along the external side walls of the second container is switched on to stimulate and agitate the larvae 108 in the second container 150. Preferably, the number of light sources placed at the bottom of the second container proximate the water outlet 160 is fewer than the plurality of light sources placed along each of the external side walls of the second container. The arrangement of the light sources 204 in this manner is to encourage the larvae 108 to wriggle towards the water outlet 160. The needle valve 156 controls the flow rate of water through the water outlet 160 and into the channel 161. The outflow of the water 111 through the water outlet 160 forces one larva 108 to be pushed (by the water current) out from the water outlet 160 and into the channel 161. The channel 161 is narrow enough for one larva to pass through. The outlet valve 162 is opened to allow the water 111 and the larvae 108 to flow through the channel 161 and into the larvae counting module 180.

The plurality of light sources 304 provided at the larvae counting module 180 stimulates the larvae 108 in the water 111 to travel through the passage 189 as shown in FIG. 4. The counter light source 183 provides an illumination across the passage 189. The illumination provides a visible tracking of the larvae 108 flowing pass the detector 182 and through the outlet valve 184. The upper portion 186 and the lower portion 188 of the larvae counting module are made of transparent material to allow light propagation through the water 111. The inlet aperture 190 provides an inlet for the inflow of water from a flush water inlet 192. The inflow of water from the flush water inlet 192 flushes the water and larvae out of the passage 189.

The downward flow of the water 111 created by the opening of the outlet valve 184 at the passage 189 forces the larvae 108 to flow through the passage 189 one at a time and flow pass the detector 182. The light sources 304 positioned at the external side walls of passage 189 provide sufficient light for a clearer detection of the larva 108 by the detector 182. The detector 182, together with the counter light source 183, detects each larva 108 that passes through the passage 189. If the detector 182 detects the one larva 108, the processor unit 194 keeps track and counts the larva. In one embodiment, the detection and counting of the larvae comprises detecting a change of intensity of the counter light source as the larva passes through the passage 189 and transmitting information about the larva to the processor unit to keep track and count the larva. The light changing includes, but not limited to, light scattering, light obscuration or direct imaging. In another embodiment, the detection and counting of the larvae comprises capturing an image of the larva passing through the passage and transmitting information about the larva to a processor unit to keep track and count the larva.

The method of the present invention further comprises placing the first container at a higher level than the second container and placing the second container at a higher level than the larvae counting module to enable gravity induced flow of water and larvae from the first container into the second container and from the second container into the larvae counting module.

The method further comprises controlling the distribution of the larvae in the larvae counter by controlling the intensity of the light sources 104, 204, 304 penetrating through the first container 100, the second container 150 and the larvae counting module 180; and the arrangement of the light sources 104, 204, 304 around the first container 100, the second container 150 and the larvae counting module 180. The distribution of the larvae includes grouping the larvae, scattering the larvae and keeping the larvae within a specific location. The scattering of the larvae includes projecting light into the water body and guiding the larvae through the aperture 106, the water outlet 160 and the passage 189 to prevent clustering of the larvae. Controlling the flow rate of the water in the larvae counter leads to regulating the flow rate of the larvae. Regulating the flow rate of the larvae leads to controlling the concentration of larvae in body of water.

In one embodiment, the printed circuit board is replaced by a flexible circuit board. The advantages of using a printed circuit board include the reduction of electrical noise and sturdy construction for surface mounted components. The advantages of using a flexible circuit board include compactness and flexibility which provides versatile installation options.

In one embodiment, the larvae counter 200 is remotely controlled. The processor unit 194 provides a communication module that is communicable with wireless technologies such as 2G, 3G, 4G, 5G, WiFi, Bluetooth, InfraRed, NFC and wired connection which provides hardware interfaces like universal serial bus (USB) connectors. The remote access provides a safe environment for users and convenience to use the larvae counter 200.

The larvae counter of the present invention can be used for counting any suitable type of water-borne larvae. Such types of larvae include, but are not limited to, mosquito larvae, fish larvae, amphibians, etc.

In the application, unless specified otherwise, the terms "comprising", "comprise", and grammatical variants thereof, intended to represent "open" or "inclusive" language such that they include recited elements but also permit inclusion of additional, non-explicitly recited elements.

The above is a description of the subject matter the inventors regard as the invention and is believed that those skilled in the art can and will design alternative embodiments that include of this invention as set forth in the following claims.

REFERENCE NUMERALS 100 first container
104 light source
106 displacement aperture
108 larvae, wriggler
110 eggs
111 water
112 water inlet
114 water inlet valve
116 larvae and water out
118 water displacement line
150 second container
152 air inlet
154 inlet valve
155 water inlet
156 needle valve
158 air
160 water outlet
161 channel
162 water outlet valve
163 openings
180 larvae counting module
182 detector
183 counter light source
184 water outlet valve
186 upper portion of larvae counting module
188 lower portion of larvae counting module
189 passage
190 inlet aperture
192 flush water inlet
194 processor unit
200 larvae counter
202 displacement spout
203 conduit
204 light source
206 first end of conduit
207 second end of conduit
208 water inlet
210 water inlet valve
304 light source

The invention claimed is:

1. A larvae counter comprising:
a first container for receiving water, eggs of insects and/or larvae, the first container having an outlet for dispensing larvae and water from the first container;
a second container in fluid communication with the first container for receiving larvae and water from the first container; and
a larvae counting module in fluid communication with the second container for receiving larvae from the second container and counting the larvae;
wherein the second container comprises a channel in fluid communication with the larvae counting module, the channel comprises a plurality of openings disposed along the longitudinal surface of the channel that is away from the second container and configured for directing larvae from the second container into the larvae counting module; and wherein the larvae counting module comprises a passage for single larva to pass through and a detector positioned proximate the passage for detecting each larva passing through the passage.

2. The larvae counter of claim 1, wherein the channel is configured to direct larva one at a time from the second container into the passage of the larvae counting module.

3. The larvae counter of claim 2, wherein the channel is connected to a water outlet of the second container positioned at the base of the second container, the channel includes an outlet valve for regulating flow rate of water through the water outlet of the second container.

4. The larvae counter of claim 1, wherein the channel has a diameter of 3 mm sufficient for a single larva to pass through the channel.

5. The larvae counter of claim 1, wherein the passage has a diameter of 1.0 mm to 6.0 mm.

6. The larvae counter of claim 1, wherein the larvae counting module comprises a funnel having an upper portion and a lower portion, the upper portion being wider than the lower portion, the lower portion defines the passage for single larva to pass through and wherein the lower portion has an open end for water and larvae to pass through and out of the larvae counter after the larvae are counted.

7. The larvae counter of claim 1, wherein the detector is an image capturing device having an image sensor, the image sensor detects and transmits information about the larva to a processor unit to keep track and count the larva.

8. The larvae counter of claim 1, wherein the detector is an optical counter having a light sensor for detecting change of intensity of light when larvae passes through.

9. The larvae counter of claim 1, wherein the larvae counting module is provided with a counter light source positioned opposite the detector for facilitating the detection of larvae passing through the passage.

10. The larvae counter of claim 1, wherein the second container further comprises a water inlet positioned at the top of the second container for receiving water and larvae from the first container.

11. The larvae counter of claim 10, wherein the second container is in fluid communication with the first container via a conduit, the conduit comprises:
a first end and a second end, the first end having a funnel mouth for receiving larvae and water from the first container and the second end is removably attached to the water inlet of the second container.

12. The larvae counter of claim 11, wherein the conduit is positioned tilted at an angle with respect to a horizontal plane for facilitating flow of water and larvae from the first container to the second container.

13. The larvae counter of claim 1, wherein the second container further comprises a needle valve for controlling air flow into the second container.

14. The larvae counter of claim 1, wherein the first container, the second container and the larvae counting module are made of glass.

15. The larvae counter of claim 1, wherein the first container is provided with at least one light source positioned at the bottom of the first container for stimulating larvae to separate from the eggs.

16. The larvae counter of claim of 1, wherein the second container is provided with a plurality of light sources positioned along the side walls of the second container and/or the bottom of the second container for controlling larvae distribution inside the second container.

17. The larvae counter of claim 1, wherein the larvae counting module is provided with at least one light source positioned along the passage.

18. The larvae counter of claim 1, wherein the first container, the second container, the channel and the lower portion of the larvae counting module defining the passage are each provided with at least one valve for regulating the flow rate of water and larvae movement from one place to another.

19. The larvae counter of claim 6, wherein the larvae counting module further comprises at least one water inlet positioned proximate to an open end of the lower portion of the larvae counting module for flushing remaining larvae in the passage out of the larvae counter.

20. The larvae counter of claim 1, wherein the first container further comprises smooth inner periphery walls.

* * * * *